United States Patent
Heinz

(10) Patent No.: US 10,603,223 B1
(45) Date of Patent: Mar. 31, 2020

(54) VACUUM COMMUTATION APPARATUS AND METHODS

(71) Applicant: Curt G. Joa, Inc., Sheboygan Falls, WI (US)

(72) Inventor: Collin Heinz, Sheboygan Falls, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 81 days.

(21) Appl. No.: 15/637,431

(22) Filed: Jun. 29, 2017

Related U.S. Application Data

(60) Provisional application No. 62/356,058, filed on Jun. 29, 2016.

(51) Int. Cl.
| | | |
|---|---|---|
| *B65H 20/12* | (2006.01) | |
| *B65G 47/84* | (2006.01) | |
| *A61F 13/15* | (2006.01) | |
| *B65H 39/14* | (2006.01) | |

(52) U.S. Cl.
CPC ...... *A61F 13/15699* (2013.01); *B65G 47/843* (2013.01); *B65G 47/848* (2013.01); *B65H 20/12* (2013.01); *B65H 39/14* (2013.01); *B65H 2801/57* (2013.01)

(58) Field of Classification Search
CPC .. B65G 47/848; B65G 47/843; B65G 47/244; B65G 29/00; B65G 21/2036; B65H 20/12; B65H 39/14; B65H 2801/57

USPC .......................................... 198/471.1, 689.1
See application file for complete search history.

(56) References Cited

U.S. PATENT DOCUMENTS

| | | | |
|---|---|---|---|
| 7,533,709 B2 * | 5/2009 | Meyer ............... | A61F 13/15699 156/516 |
| 7,987,964 B2 * | 8/2011 | McCabe ........... | A61F 13/15764 198/471.1 |
| 8,016,972 B2 | 9/2011 | Andrews et al. | |
| 8,172,977 B2 | 5/2012 | McCabe et al. | |
| 9,283,683 B2 | 3/2016 | Andrews et al. | |
| 2005/0275148 A1 * | 12/2005 | Beaudoin .......... | A61F 13/15764 271/10.01 |
| 2007/0074953 A1 * | 4/2007 | McCabe ........... | A61F 13/15764 198/377.08 |
| 2010/0326796 A1 * | 12/2010 | Walsh ............... | A61F 13/15764 198/579 |
| 2014/0251764 A1 * | 9/2014 | Gieser .................. | B41F 21/102 198/689.1 |
| 2018/0362266 A1 * | 12/2018 | Schneider, I .......... | B65G 29/02 |

* cited by examiner

*Primary Examiner* — James R Bidwell
(74) *Attorney, Agent, or Firm* — Ziolkowski Patent Solutions Group, SC

(57) ABSTRACT

The present invention provides a method and apparatus for a transporting a discrete element, by activating a discrete vacuum zone on a puck at or before an acquisition, rotating the puck about an axis (and optionally twisting the puck), and deactivating the discrete vacuum zone at a deposition point, through tightly controlled piecewise vacuum porting particularly in applications where vacuum commutation length changes in radial direction.

20 Claims, 6 Drawing Sheets

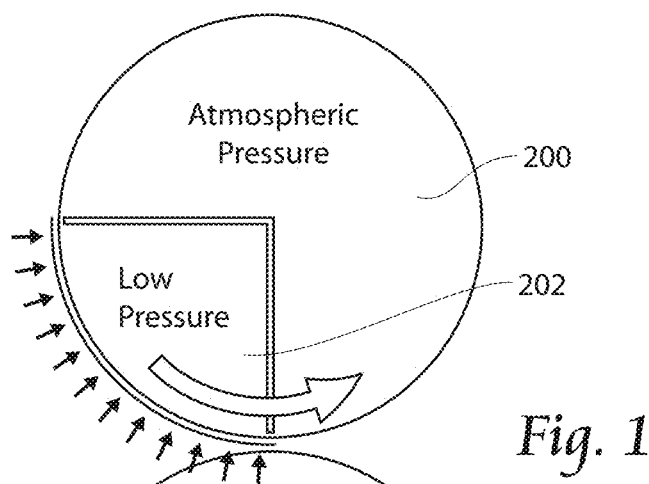
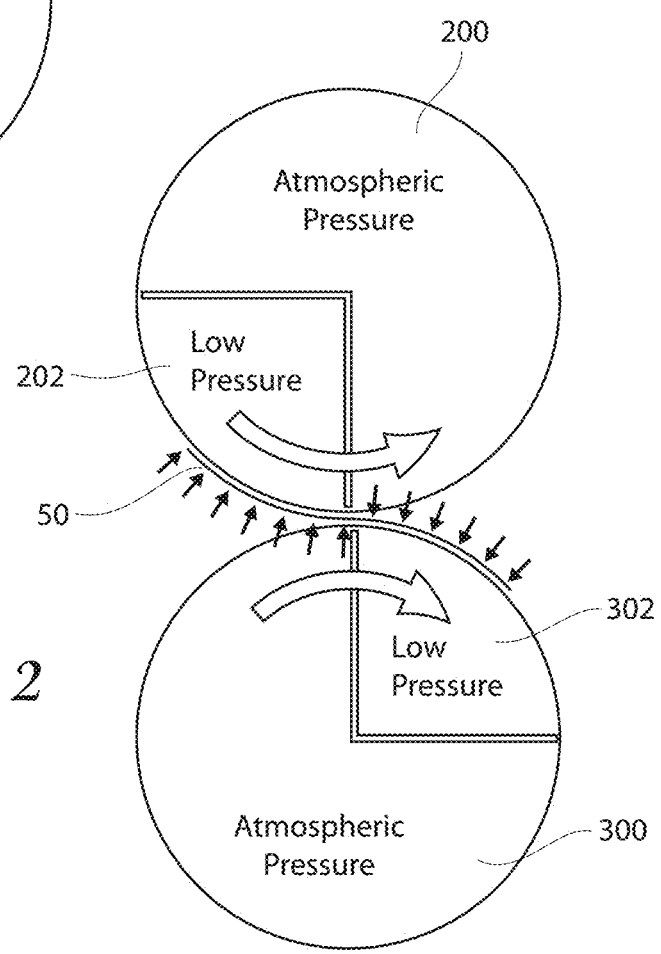
Fig. 1
Fig. 2

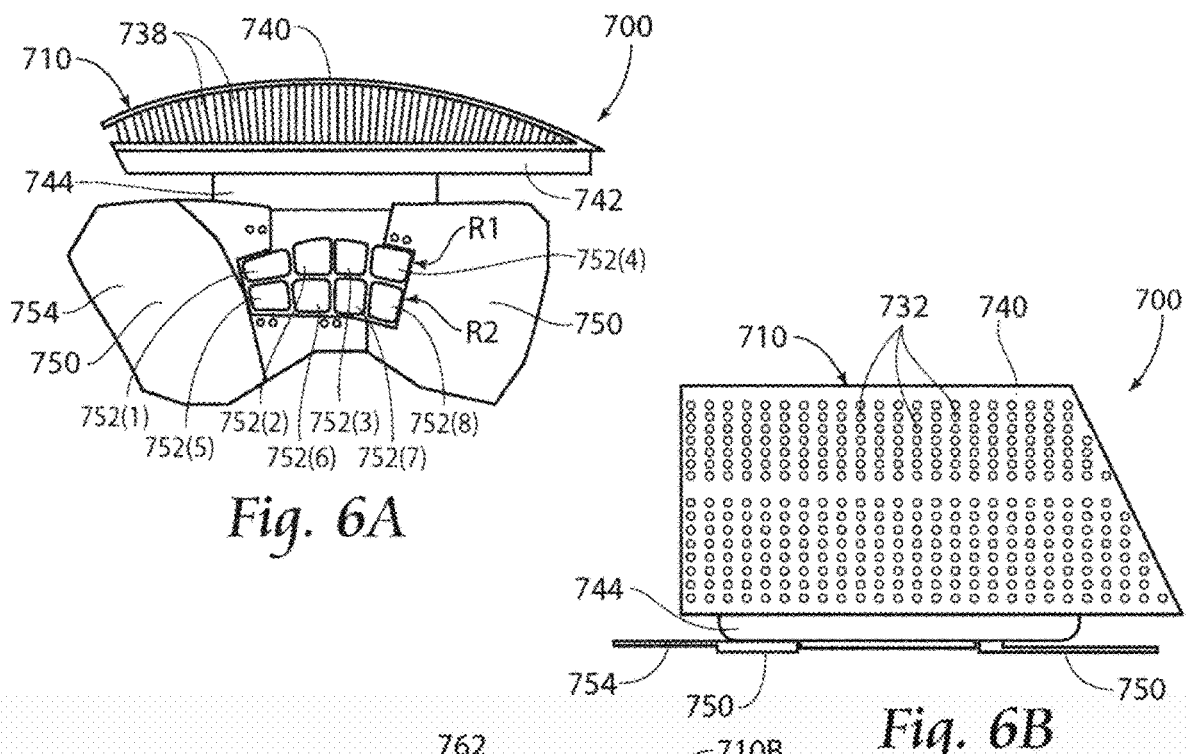
Fig. 6A
Fig. 6B
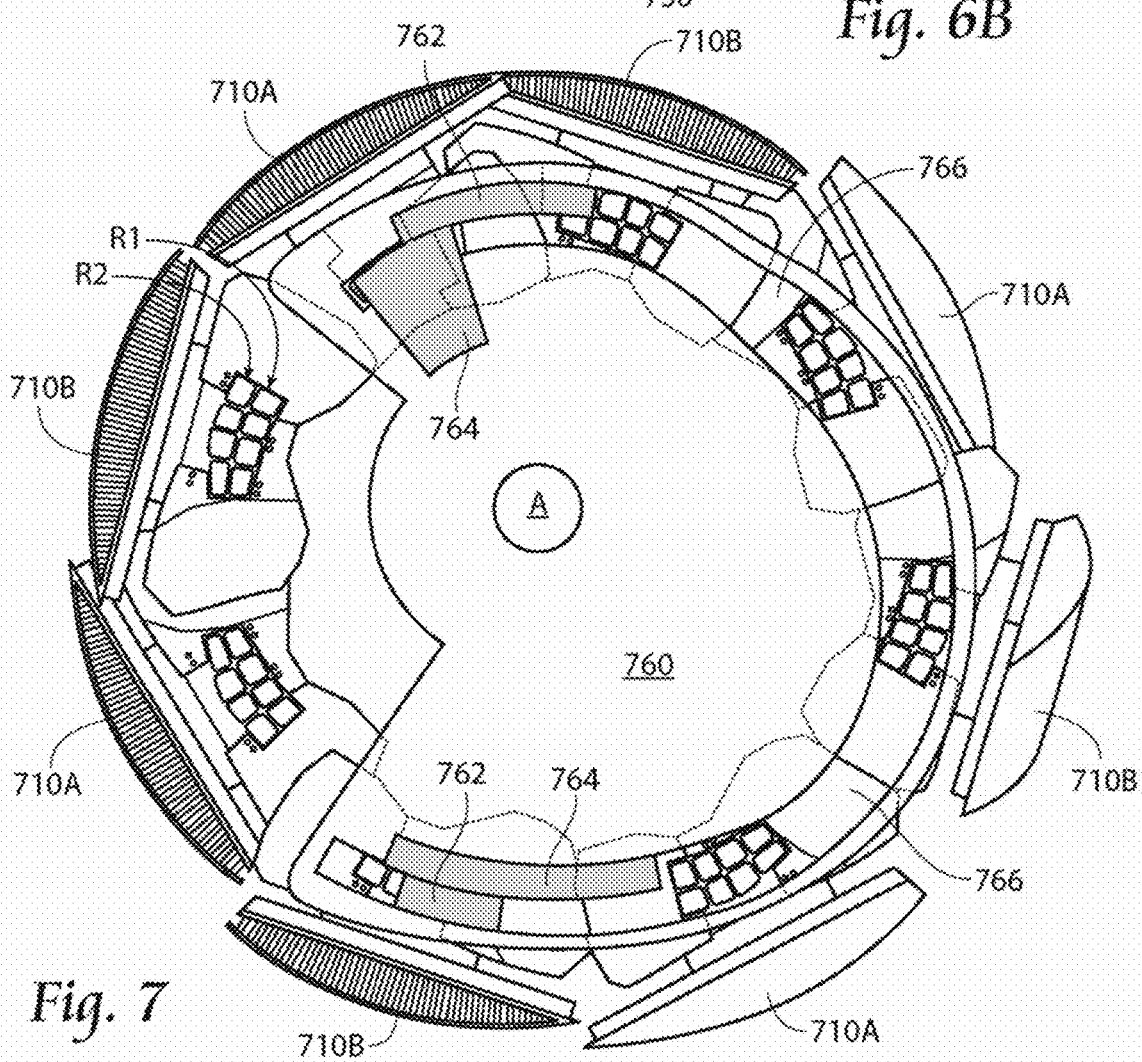
Fig. 7

VACUUM COMMUTATION APPARATUS AND METHODS

RELATED APPLICATION

This application claims the benefit of U.S. Provisional Patent Application Ser. No. 62/356,058, filed 29 Jun. 2016.

BACKGROUND OF THE INVENTION

The present invention relates to disposable hygiene products and more specifically, to methods and apparatuses for processing disposable hygiene products such as baby diapers, adult diapers, disposable undergarments, incontinence devices, sanitary napkins and the like.

More specifically, the invention relates to a novel vacuum commutation system to pucks or other structures. Vacuum is used in many parts of a diaper manufacturing process. For instance, during pulp core formation, vacuum draws pulp fibers into forming pockets on a core forming drum. Elsewhere along the manufacturing process, vacuum is used. For instance, a common method of applying discrete pieces of one web to another is by use of a slip-and-cut applicator. A slip-and-cut applicator is typically comprised of a cylindrical rotating vacuum anvil, a rotating knife roll, and a transfer device. In typical applications, an incoming web is fed at a relatively low speed along the vacuum face of the rotating anvil, which is moving at a relatively higher surface speed and upon which the incoming web is allowed to "slip". A knife-edge, mounted on the rotating knife roll, cuts a off a segment of the incoming web against the anvil face. This knife-edge is preferably moving at a surface velocity similar to that of the anvil's surface. Once cut, the web segment is held by vacuum drawn through holes on the anvil's face as it is carried at the anvil's speed downstream to the transfer point where the web segment is transferred to the traveling web. Vacuum can also be used in vacuum conveyors.

Some components of disposable products such as ears, or extension panels, require transportation and deposition by a vacuum puck. For instance, in U.S. Pat. No. 8,016,972, assigned to the same assignee as the present invention, ear webs are severed into individual ears, and rotated while held by a vacuum puck, to be applied to a traveling web such as a chassis web.

An ear is a component of a diaper that is grasped and pulled around the waist of a wearer. Typically, ears are secured to the diaper at a first end, and a second free end is typically equipped with securing means, such as a pressure sensitive adhesive, or hook and loop material. As a user grasps an ear and pulls the ear, elasticity provided about the waist region of the diaper allows the free end to be snugly pulled about the waist of a wearer, and coupled to the diaper. Ears can be rectangular or made of irregular shapes.

Typical vacuum pucks used in the prior art have rows of vacuum holes which are fed by cross-drilled ports, each being exposed to the source of vacuum by commutations, as the ports move into a zone of negative pressure in a stationary manifold. Such a configuration serves to apply vacuum sequentially and piecewise (vacuum application is discretized) to each successive row of holes. Such a configuration is shown in U.S. Pat. No. 7,533,709, incorporated herein by reference. At high speeds, it has been found that air entering the vacuum ports is drawn across an article carrying face of the puck, and the air drawn into the ports can adversely impact control over the discrete components by causing misalignment, folding or other loss of total control.

Continual improvements and competitive pressures have incrementally increased the operational speeds of disposable diaper converters. As speeds increased, the mechanical integrity and operational capabilities of the applicators had to be improved accordingly. The prior art is quite successful when processing full-width or symmetrical webs using vacuum, and vacuum is nearly universally used in diaper production. However, as speeds have increased in manufacturing, so too has vacuum demand. Along with significant increase in vacuum demand comes the expense of powering convention vacuum forming techniques, and the noise associated with traditional vacuum pumps.

The disclosed invention provides an apparatus which can provide a better solution for tightly controlled zones of vacuum commutation. The vacuum can be used for whatever purpose desired, including maintaining control over diaper webs or discrete portions of diaper webs, including sections of various shapes, and to decrease reliance on traditional vacuum generation.

SUMMARY OF THE INVENTION

The present invention provides a method and apparatus for providing a zoned or discretized vacuum commutation structure for creating a timed zone of vacuum on an article carrying surface of a structure such as a puck structure. Tightly controlled vacuum porting can be supplied to specified zones at a carrying surface for a web or a portion of a web, and is particularly well suited in applications where vacuum commutation length changes in a radial direction.

At an acquisition point, a series of vacuum manifold ports are exposed in a desired sequence to vacuum, activating vacuum at an intended zone of an article carrying surface of a puck. The article carrying surface of a puck receives the discrete object at speed to rotate the discrete object into deposition position, at which point a deposition sequence of vacuum shutoff is initiated on the article carrying surface of the puck, leaving the article to be transported free to be placed, deposited, or secondarily transported as desired (for instance by depositing the article to be transported onto a carrier web, or onto a vacuum conveyor).

A vacuum porting system is disclosed comprising an article carrying body comprising an article carrying surface, said article carrying body rotating about an axis; a first vacuum commutation zone on said article carrying surface; a second vacuum commutation zone on said article carrying surface, spaced apart from said first vacuum commutation zone in a machine direction; a first vacuum port coupled to said first vacuum commutation zone; a second vacuum port coupled to said second vacuum commutation zone; said first and second vacuum commutation zones at a variable distance from said axis. The system can further comprise said first vacuum port at a first distance from said axis, and said second vacuum port at a second distance from said axis, said second distance greater than said first distance. In a preferred embodiment, said vacuum ports are coupled to said vacuum commutation zones by a vacuum port manifold.

Also disclosed is a vacuum porting system comprising an article carrying body comprising an article carrying surface, said article carrying body rotating about an axis; a plurality of vacuum commutation zones on said article carrying surface; a first array of vacuum ports, said vacuum ports of said first array coupled to at least one of said vacuum commutation zones; a second array of vacuum ports, said vacuum ports of said second array coupled to at least one of said vacuum commutation zones; said first and second arrays of vacuum ports spaced at different radial distances from said axis.

Also disclosed is a vacuum manifold having an inner surface and an outer surface, said vacuum manifold further comprising a vacuum manifold channel, said vacuum ports selectively exposed to said vacuum manifold channel, and further comprising a blinder carried by said article carrying body, said blinder coupled to said inner surface of said vacuum manifold during rotation of said article carrying body; and said vacuum porting system further comprising a series of article carrying bodies rotating about said axis, said article carrying surfaces extending from a first distance to a second distance from said axis, and a plurality of said vacuum ports and said blinders covering said vacuum manifold channel; and further comprising a source of vacuum coupled to said outer surface of said vacuum manifold, which can present a variable width across its channel. First and second arrays of vacuum ports are provided, with increasing and decreasing radial distances from said axis during rotation of said article carrying bodies about said axis.

BRIEF DESCRIPTION OF THE DRAWINGS

FIG. 1 is a demonstrative side view of rotating bodies and air flow patterns;

FIG. 2 is a demonstrative side view of rotating bodies and air flow patterns;

FIG. 6A is a side view of a puck of the present invention, with dedicated vacuum commutation ports corresponding to zones on an article carrying surface of the puck;

FIG. 6B is a top view of the puck of FIG. 6A, showing the article carrying surface of the puck, communicatively coupled through a vacuum port manifold, and blinders to assist in proper vacuum commutation and to prevent vacuum loss;

FIG. 7 is a system of rotating pucks of FIGS. 6A and 6B, rotating about an axis, and radiating from said axis during rotation;

DESCRIPTION OF THE PREFERRED EMBODIMENT

Figure 3:
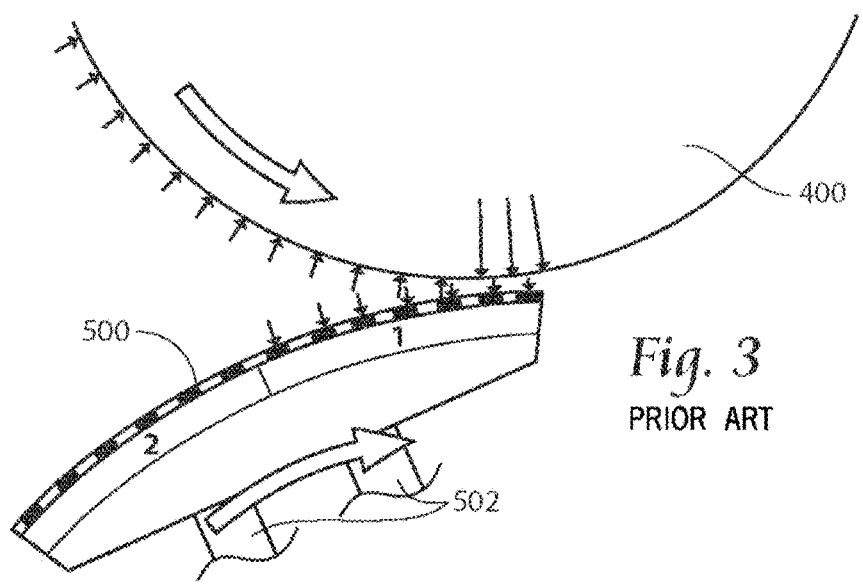
FIG. 3 is a side view of a two-zoned puck structure.

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Referring now to FIG. 1, a demonstrative side view of rotating bodies 200 and 300 and air flow patterns is shown. Upstream of the tangent between the two rolls 200 and 300, air is being driven into the low pressure zone 202 of the upper drum 200. Due to the rotation of the drums 200 and 300 and the applied vacuum forces, low pressure is created between the drums 200 and 300. Atmospheric air can enter the system from the upstream side of tangent point of the drums 200 and 300, and some air can rush downstream from the higher pressure zone towards the downstream side of the transfer point (not shown). Because so much air is drawn in to create the low pressure zone in prior art vacuum system design, air velocity can undesirably cause patches carried by the drum (not shown) to behave erratically, and lead to flipping over of leading or trailing edges. It has been found that even a small change in the air conditions at the patch to create imperfections and unrepeatability. To solve this problem, the system of the present invention limits the amount of airflow in the zone on the upstream side of the tangent part of the rolls 200 and 300, so the system does not undesirably induce pressure, causing air to inrush. Because the bottom drum 300 of the present invention is supplied at least in part at atmospheric pressure, air can flow from the interior region of the bottom drum 300 to satisfy the need for air in the low pressure area 202 of the top drum 200.

FIG. 2 is a demonstrative side view of rotating bodies 200 and 300 and air flow patterns, with this configuration showing two low pressure zones 202 and 302, one in each of the top and bottom rotating drums 200 and 300 respectively. A patch 50 is shown being transferred from the top drum 200 to the bottom drum 300, but it is understood that in an operating system, the handoff of the patch 50 is going to be upstream handoff to a downstream unit in the machine direction.

To optimize the air flow of the system and minimize undesirable air flow patterns, it has been found advantageous to avoid locating low pressure zones 202 and 302 opposite of one another in a rotating system. Avoiding adjacent low pressure zones allows atmospheric air to flow into the low pressure zones 202 and 302 as intended, without undesirable turbulence that could be transmitted to the carried web or patch.

As shown in FIG. 2, low pressure zone 202 on the top drum 200 leads up to the tangent point between the top drum 200 and bottom drum 300, and a low pressure zone 302 trails the tangent point on the bottom roll 300. It has been found that this configuration minimizes the undesirable inrush of air from the upstream side of the tangent point. Downstream of the tangent point, the interior (center) of the top drum 200 is exposed to atmospheric pressure, and this zone assists to satisfy air demand into the low pressure zone 302 of the bottom drum 300. Conversely, upstream of the tangent point, the interior (center) of the bottom drum 300 is exposed to atmospheric pressure, and this zone assists to satisfy air demand into the low pressure zone 202 of the top drum 200. The general principle is that it has been found advantageous in material handling to avoid low pressure zones opposite of one another while handling a web or a patch 50.

Referring now to FIG. 3 is a side view of a prior art puck structure 500 is shown. In this configuration, ambient air leaves a low pressure zone upstream of the tangent between puck 500 and rotating drum 400. Because surfaces of both puck 500 and drum 400 are open to a vacuum chamber, this results in a low pressure zone between surfaces, which undesirably cause air to inrush from the sides and ends of the surfaces. The ambient air inrush from between where air is drawn into drum 400, and where air is drawn into puck 500 can disturb a patch on a drum 400 or puck as the patch is transferred. In the current system, at the moment of transfer, and at the transfer point, a transfer assist sequence (shown in arrows leaving the interior of drum 400) assists patch or web transfer from drum 400 onto puck 500 (or off of a puck as the case may be) by using a blast of pressurized air at that specific location (the transfer point) to blow the patch off the drum 500 and onto the puck 400 receiving the patch. The pressurized air from drum 400 can undesirably blow into the puck 500, and the extra air movement challenges the efficacy of the transfer or patch handoff.

In some prior art puck systems, two zones 1 and 2 are created at the puck surface, so that vacuum to these zones 1 and 2 can be independently controlled. Zone 1 can have applied vacuum while zone 2 has no applied vacuum. Alternatively, zone 2 can have applied vacuum while zone 1 has no applied vacuum. The on/off sequence is principally dictated by whether the puck 500 is receiving a patch or handing off a patch. It is desirable in certain handoff or receiving operations to, at a leading edge of the puck 500 in zone 1, apply vacuum to receive the leading edge of the received patch. But when it comes time to hand off the patch to the next equipment downstream, it is desirable to turn vacuum off of zone 1 to hand the patch off and relinquish control of the patch to the next piece of equipment, while retaining the patch with vacuum applied in zone 2. The desired blowoff to assist patch handoff can undesirably minimize the vacuum present in the puck 500 in zone 1 at that point.

Certain aspects of the present invention follow a passive or non mechanical-valve solution. By increasing the number of zones, more accuracy and precision of zone timing of on/off relative zone to zone can be achieved. Vacuum supply zone spacing might be 20 degrees wide whereas corresponding puck zone patch length may be 45 degrees. This mismatch of supply vs. puck angle creates phase/timing variation over time.

In conventional vacuum puck designs, the pucks have cross machine direction air chambers that are connected to the surface of the puck 500. As the puck 500 travels, the air chambers move between high and low pressure zones of a vacuum manifold, and this results in air flowing into or out of the surface of the puck 500. This airflow and the associated pressure differentials will either cause a material patch to be attracted or repelled from the puck surface 500.

Still referring to FIG. 3, one shortcoming of the prior art is that ports 502 which commute vacuum to puck 500 are located remotely from the puck 500. The control for turning vacuum on or off at zones 1 and 2 is therefore remote from the puck 500. This remote arrangement undesirably creates lag time for high speed switching of vacuum on and off in zones 1 and 2. Because some of the turner pucks of the prior art, for instance those disclosed in U.S. Pat. No. 8,172,977, rotate both in the machine direction and cross machine direction at the same time, it is impractical to use a conventional combination of a side vacuum manifold aligning with cross machine direction air chambers. Therefore, the air passages between the puck 500 and the vacuum chamber are routed through the center of the pucks 500. This results in relatively long airflow passage ways between the surface of the puck 500 and the vacuum supply manifold (not shown). This restricts the speed at which the direction of airflow at the surface of the puck 500 can be reversed. The remoteness of the vacuum manifold from the puck 500 is difficult to implement with pucks with multiple discrete zones that require quick changes in airflow direction.

Figure 4:
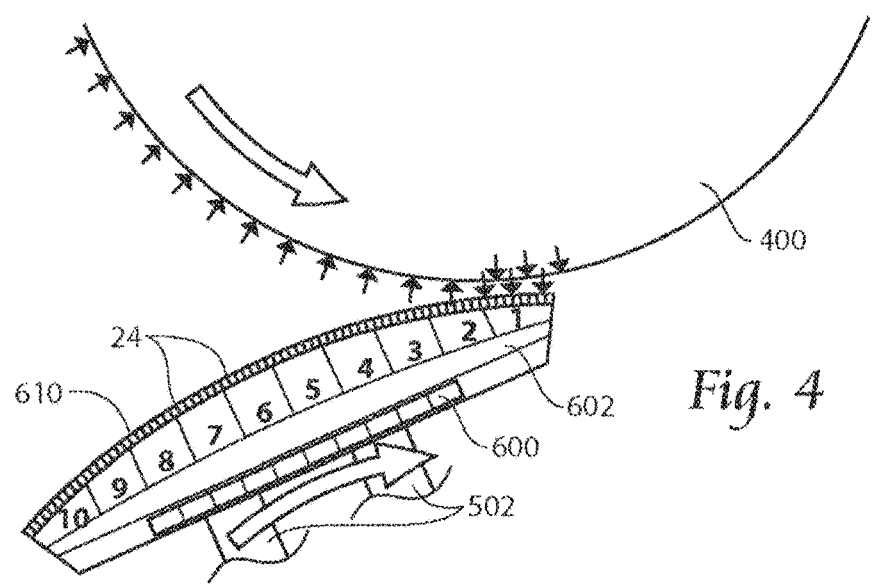
FIG. 4 is a side view of a puck structure with micro vacuum commutation ports and zoned vacuum commutation porting, in this example showing a plurality of zones (ten)
Figure 5:
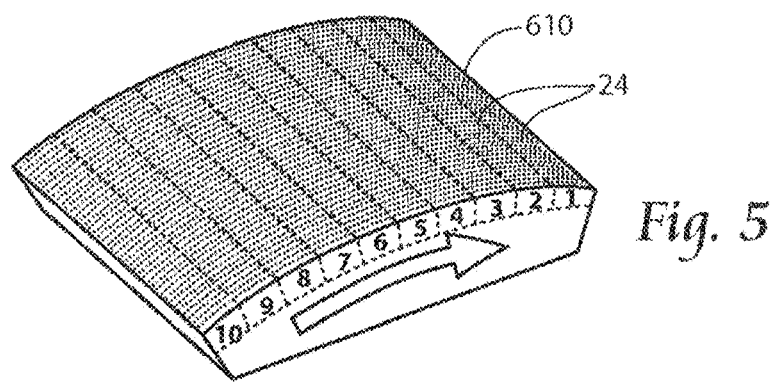
FIG. 5 is a perspective view of a puck for carrying discrete portions of a web, the puck with micro vacuum commutation ports and optionally valved and zoned vacuum commutation porting, in a passive system only a half a valve is shown.

Referring now to FIG. 4, a side view of a puck structure 610 with zoned vacuum commutation porting is shown. As with the example shown in FIG. 2 of two adjacent vacuum rolls that transfer a patch of material from one roll to the other roll, the same airflow surface improvements can be made to a system that replaces one or both of the full rolls with vacuum pucks 610 that behave as partial rolls.

Instead of two zones 1 and 2 of the system shown in FIG. 3, the puck 610 of FIG. 4 can be made with multiple zones, 1-10 or more for instance. Zones 1-10 can either be open to the vacuum chamber (not shown) through ports 502 or open to the atmosphere. With the segmented vacuum zone 1-10 configuration on the puck 610, the system requires far less (if any) blow off pressure from the drum 400. As the puck 610 passes the tangential point, each of the zones 1-10 are selectively turned on in an acquisition sequence, in order to gain control of the patch as the puck 610 rolls past the drum 400.

A rotating valve disk 600 is used to rapidly control the application of vacuum air to each individual zone 1-10 in a controlled way. By sequential vacuum engagement, the undesirable low pressure zone at the transfer point between drum 400 and 610 is minimized if not eliminated, and there is therefore less turbulence or disruption of a carried patch at that point. Incorporating a valve mechanism 600 that can quickly switch airflow passages between a vacuum supply chamber and atmosphere in the puck 610 reduces the level of the air passage lengths to a level that will enable adequately rapid response. This allows for on/off times of zones 1-10 to be nearly instantaneously controlled because of the proximity between the vacuum commutation and the vacuum surface of the puck 610. This proximity also enables a rotating puck 610 to have multiple air flow zones 1-10 which can be controlled to switch the airflow direction at the surface of the puck 610. By using multiple zones 1-10, airflow at the surface of the puck 610 can be optimized to closely approximate the airflow characteristics of a two roll system shown in FIG. 2.

By locating the rotating valve disk 600 or other form of vacuum control inside of the puck 610 assembly itself, this puts the mode of control into the puck 610, and minimizes lag time for on/off operations. Zone control in the puck 610 is adjacent to the puck surface.

Still referring to FIG. 4, internal air passages 602 from valve disk 600 are used commute vacuum from ports 502 to the surface of puck 610.

In a preferred embodiment, use of a blinder 750 and blinder recess 754 of the present invention advantageously minimizes moving parts. This is advantageous because many moving parts increase wear and add complexity of unit. Referring now to FIG. 6A, a side view of a puck system 700 of the present invention is shown, with dedicated vacuum commutation ports 752-1-752-8, corresponding to zones on an article carrying surface 740 of a puck 710. Referring first to puck 710, one type of puck that may be used is of the type disclosed in U.S. Pat. No. 9,283,683, disclosed to the same assignee as the present invention, and incorporated herein by reference. The puck system 700 provides a method and apparatus for providing a zoned vacuum commutation structure for creating a timed zone of vacuum on article carrying surface 740 of puck 710. By using a vacuum generation source (not shown), air is drawn first through commutation ports 732 on the article carrying surface 740 (FIG. 6B showing a top view), next through commutation pipes 738, next through a divided manifold header 742, next through a manifold passage 744, and next through dedicated vacuum commutation ports 752-1-752-8. It is the vacuum that retains discrete pieces on the article carrying surface 740 of puck 710.

A nested blinder 750 with a blinder recess 754 is provided to shield and limit where vacuum will be communicated, to assist in proper vacuum commutation and to prevent vacuum loss (described later).

Referring now to FIG. 7, a system of rotating pucks of FIGS. 6A and 6B is shown, rotating about an axis A, and radiating from said axis during rotation. In the embodiment shown, but not by way of limitation, two types of pucks can be provided, non-rotating pucks 710A and rotating pucks 710B. The non-rotating pucks 710A can carry ears (not shown) that do not require rotation into a proper orientation, and the rotating pucks 710B can carry ears requiring rotation into a proper orientation (see, e.g. FIG. 1, U.S. Pat. No. 9,283,683, incorporated by reference). As the pucks 710A and 710B go through their rotation about axis A, ears can picked up from an upstream ear die/anvil station (not shown) and rotate about axis A, while every rotating puck 710B also revolves around its own radius during rotation. A similar puck arrangement and operating sequence explaining the rotation of the pucks and an acquisition and deposition system in which the present invention can be used, for instance, is shown in FIGS. 9-15 of U.S. Pat. No. 8,016,972, and described in the related text, U.S. Pat. No. 8,016,972 incorporated by reference. A similar system is shown in FIG. 8A of U.S. Pat. No. 8,172,977, also incorporated by reference. In those systems, a discrete ear piece is acquired by an individual puck 234A or 234B at an acquisition point at the 12 o'clock positions of puck assemblies 200R and 200L, and deposited at a deposition point at the 6 o'clock positions of puck assemblies 200R and 200L.

Figure 8:
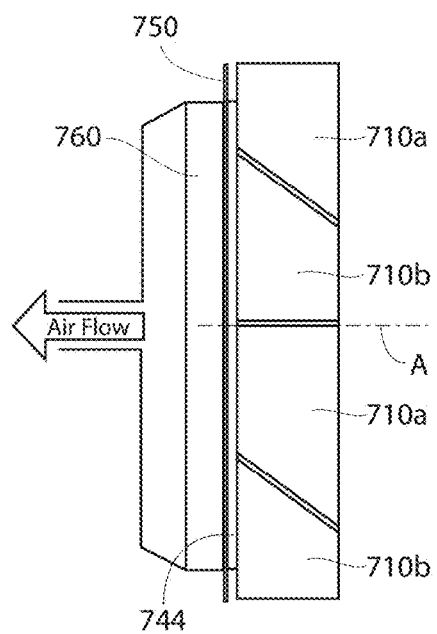
FIG. 8 is a side view of vacuum application to the system.

Referring again to FIG. 7, a shaped internal manifold 760, with a vacuum channel 766, is coupled to a source of vacuum (FIG. 8 is a side schematic view of vacuum application to the system), such that vacuum is commuted through vacuum channel 766 of the shaped internal manifold 760, but preferably not to areas external to the shaped internal manifold 760. As pucks 710A and 710B are rotated about axis A, dedicated vacuum commutation ports 752-1-752-8 of each puck 710A and 710B encounter the vacuum channel 766 sequentially. The sequence in which the dedicated vacuum commutation ports 752-1-752-8 encounter the channel 766 can be controlled by stop blocks 762 and 764, which can be moved radially, or resized to change timing and sequence of when dedicated vacuum commutation ports 752-1-752-8 encounter channel 766.

Still referring to FIG. 7, each puck 710A and 710B carries a nested blinder 750 with a blinder recess 754. A nested blinder wing 750 of an upstream puck 710 is slidably carried by a blinder recess 754 of an adjacent nested blinder 750. Together, adjacent nested blinders 750 serve to cover or block the vacuum channel 766 from the ingress of air external to the system 700. This blockage of the ingress of the air external to the system 700 shields and limits where vacuum will be communicated, assist in proper vacuum commutation through only dedicated vacuum commutation ports 752-1-752-8 within channel 766, thereby preventing vacuum loss. Blinders 750 allow pucks 710 to change radial position without loss of vacuum about the periphery of dedicated vacuum commutation ports 752-1-752-8, without blinders it is possible that the areas between dedicated vacuum commutation ports 752-1-752-8 of successive pucks 710A and 710B would allow vacuum to leak from that area.

Referring particularly now to the shape of the channel 766, in a preferred embodiment, the channel 766 is configured to have a curvature to correspond with extension and rotation of pucks 710. The shape of particularly dedicated vacuum commutation ports 752-2 and 3, for instance, can be profiled to match the curvature of channel 766, such that the entirety of dedicated vacuum commutation ports 752-1-752-8 remains within channel 766, and preferably no portions of dedicated vacuum commutation ports 752-1-752-8 are blocked by the periphery of channel 766 to retain full air flow through the dedicated vacuum commutation ports 752-1-752-8.

Figure 9:
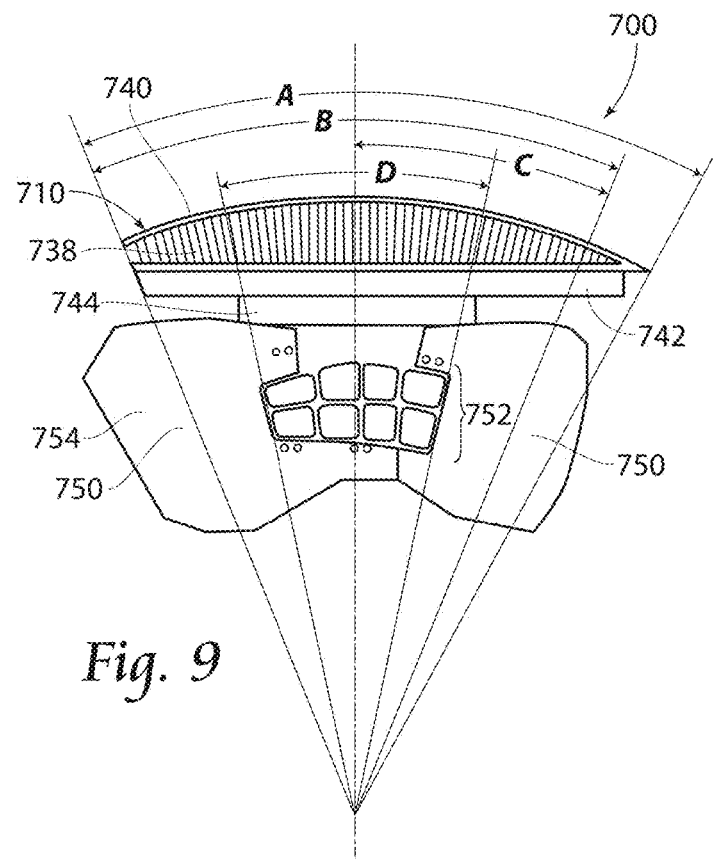
FIG. 9 is a side view of a puck and vacuum commutation zoning scheme.
Figure 10:
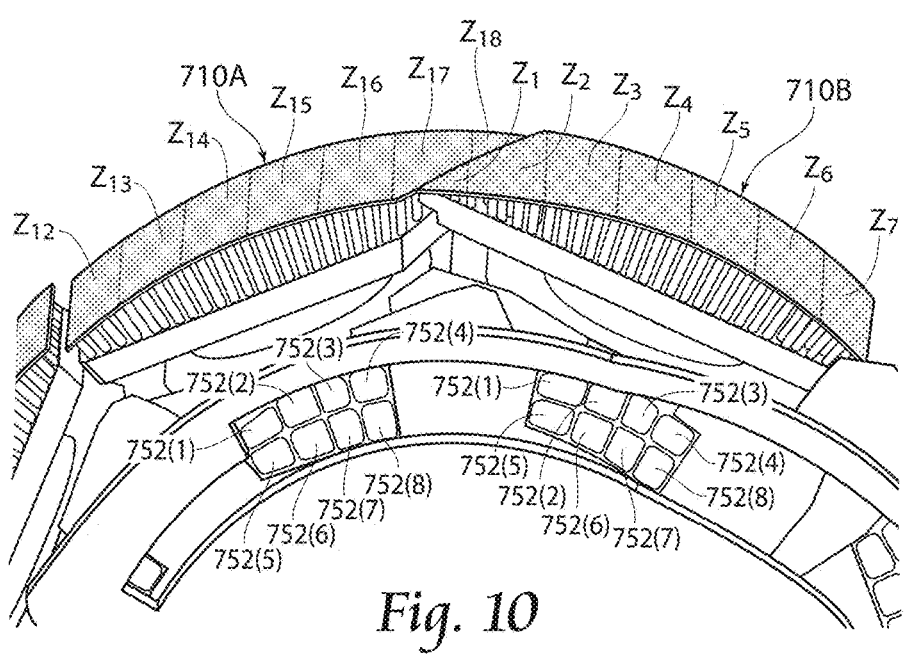
FIG. 10 is a perspective view of the system in use.

Referring now to FIG. 9, as an angle of vacuum supply D matches puck angle of surface D=1, additional rows of vacuum allows a closer approximation of a ratio to near 1. For instance, using a single row of vacuum ports (not shown), there would be D degrees (for instance 24 degrees) and an angle of the puck surface of A degrees (for instance 50 degrees) so the ratio would equal 0.48. In an embodiment with an additional row of vacuum ports as shown in FIG. 9, D degrees can be multiplied by 2, such that 48 degrees total of vacuum commutation through a rotation could be accommodated. Therefore, the ratio of 48 degrees of vacuum supplied across the 2 rows (24 degrees each) to 50 degrees is close to 1. Because, in preferred embodiments the pucks 710a have a shorter side and a longer side (in addition to a shorter leading edge, compared to a longer leading edge, or vice versa) as seen in FIG. 9, an angle B, the minimum angle from the leading edge to the trailing edge will be less than an angle A, the maximum angle from the leading edge to the trailing edge. Similarly, angle C, the minimum rotational angle from the midpoint of the vacuum commutation zone 752 to the leading or trailing edge is provided.

Figure 11:
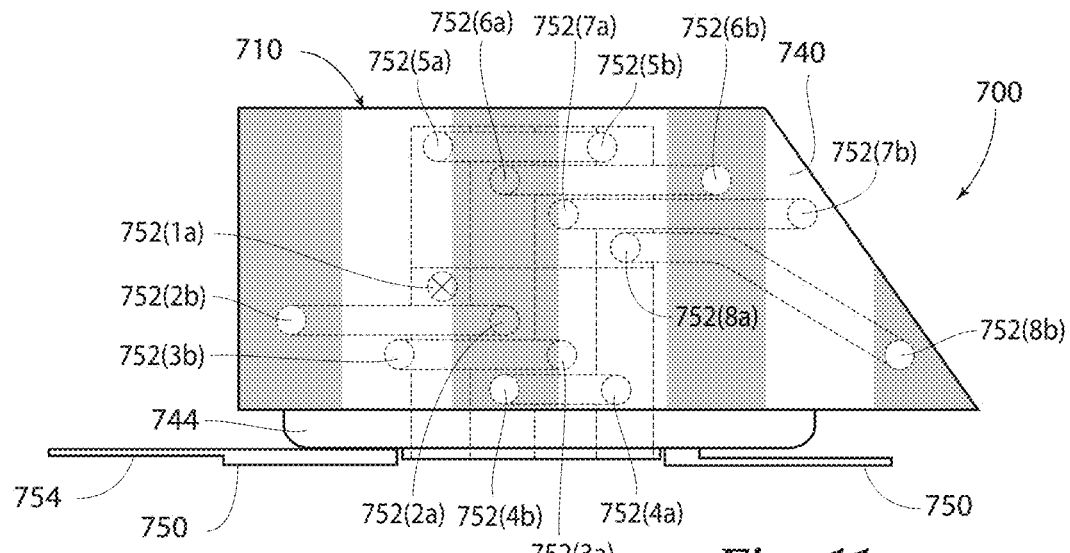
FIG. 11 is a top view of the puck of FIGS. 6A and 6B, with vacuum commutation zones being vacuum supplied by channels in the manifold coupled to the dedicated vacuum commutation ports.
Figure 12:
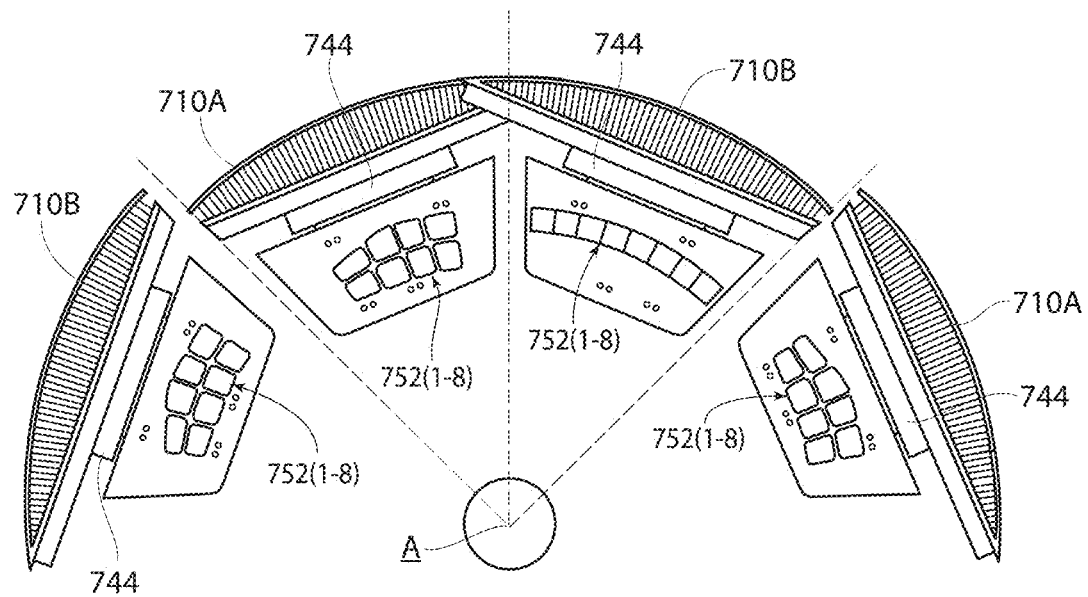
FIG. 12 is a side view of alternate dedicated vacuum commutation port arrangements.

Referring now to FIG. 11, a top view of the puck of FIGS. 6A and 6B is shown. Shaded portions represent areas or zones where commutation ports 732 (shown in FIG. 6B, but not shown in this figure for clarity) of article carrying surface 740 can be independently controlled. Of course more or less zones can be provided by changing the number and arrangement of commutation ports 732, and their associated dedicated vacuum commutation ports 752-1-752-8. An increased number of separate vacuum feeds (through dedicated vacuum commutation ports 752-1-752-8) allows for a finer resolution of vacuum on/off control, and the discretizing of puck can be tailored according to user preference. In different embodiments shown in FIG. 12, a side view of alternate dedicated vacuum commutation port arrangements vacuum commutation ports 752-1-752-8, in either a one-row arrangement R1, or a two row arrangement, R1 and R2. It can be seen that adding 2 rows of supply vacuum ports allows closer supply vs Vacuum supply zone. This mismatch of supply vs. puck angle creates phase/timing variation over time.

Each of dedicated vacuum commutation ports 752-1-752-8 is associated with a zone, 1-8 respectively. Alternatively, and in a preferred embodiment of the present invention, the number of vacuum commutation ports 752-1-752-8 can be greater than the number of zones 1-7 at the of article carrying surface 740. Still referring to FIG. 11, an unused port (one of vacuum commutation ports 752-1-752-8 not coupled to a dedicated zone) allows for proper sequencing, in particular when a zones location has no corresponding symmetric 'pair' about rotating axis. When pucks are different configurations, such as pucks 710A and 710B of FIG.

10, unused ports corresponds to a non-symmetric puck orientation. Such could be the case where the pucks rotate about their axis as described in U.S. Pat. No. 8,016,972 or 8,172,977. In the processes of U.S. Pat. No. 8,016,972 or 8,172,977 (all incorporated by reference), this occurs at web or discrete piece entry to the system. Orientations are matched during exit from the system. When the number of vacuum commutation ports 752-1-752-8 is greater than the number of zones 1-7 at the of article carrying surface 740 (each shaded area, as shown in FIG. 11), one of the vacuum commutation ports 752-1-752-8 will be a "dead port", not associated with a zone. In the embodiment shown in FIG. 11, vacuum commutation port 752-1 is shown as a "dead port" associated with 752(1a) and not coupled to a surface zone. In a different puck arrangement, such as 710B, with the pointed end trailing, vacuum commutation port 752-8 would be a "dead port" associated with 752(8a) and not coupled to a surface zone.

Manifold header 742 (see FIG. 6A) can be divided and compartmentalized such that air is drawn through the commutation ports 732 of a specified zone and into a dedicated portion of manifold header 742. Referring to FIG. 11 again, when it is desired to apply vacuum to a specific zone, the zone to the farthest right in the figure for instance, vacuum commutation port 752-8 (see FIG. 13A) is exposed to vacuum within vacuum channel 766, "turning on" the associated zone in FIG. 11 by activating channel 752-8A within manifold passage 744 (which, for rotating pucks 710B, also serves as a turning disk, about which the article carrying surface 750 can spin), extending between vacuum commutation port 752-8 within the channel 766 and channel 752-8B within manifold header 742.

Figure 13A:
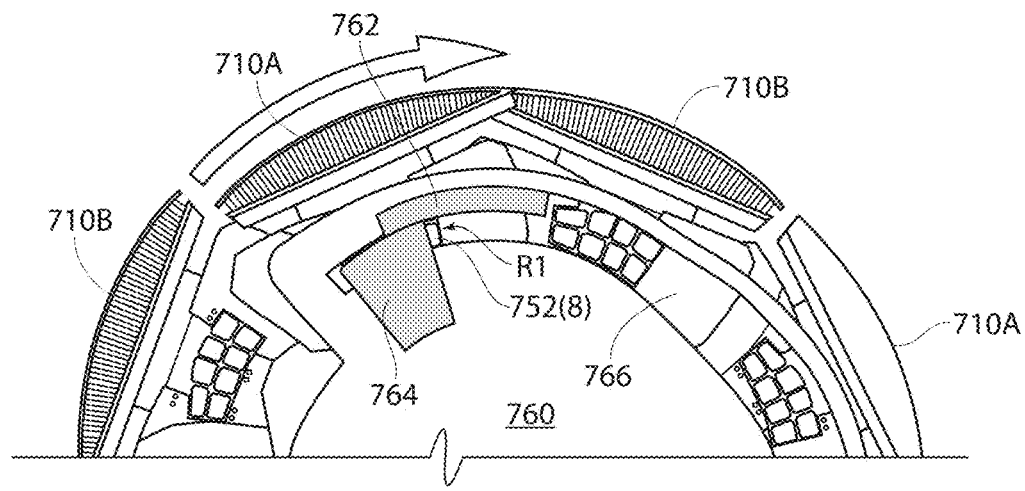
FIGS. 13A-13C are a side view of a sequence of dedicated vacuum commutation ports passing a series of stop blocks within an interior vacuum manifold to expose the dedicated vacuum commutation ports in a desired pickup and vacuum engagement sequence.
Figure 13B:
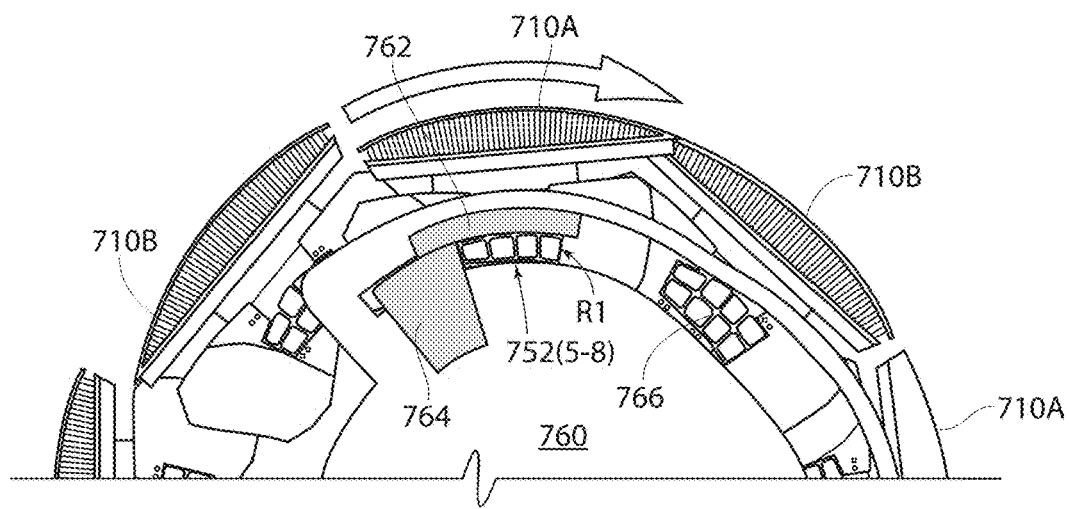
Figure 13C:
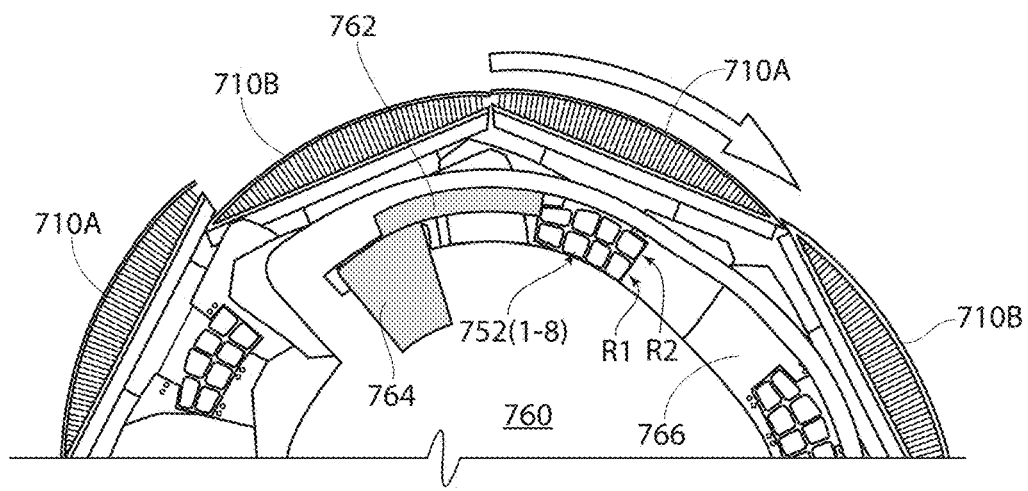

Referring now to FIGS. 13A-13C, a side view of a preferred activation sequence of vacuum commutation ports 752-1-752-8 (and thus, their associated zone at the article carrying surface 740) is shown. A pair of stop blocks 762 (outer) and 764 (inner) is used if a two row (R1 and R2) port configuration is chosen. Stop block 762 is sized and configured to cover, momentarily during revolution, vacuum commutation ports 752-1-752-4 of row R2, keeping zones associated with those ports "turned off". Stop block 764 is sized and configured to cover, momentarily during revolution, vacuum commutation ports 752-5-752-8 of R1, also keeping zones associated with those ports "turned off." In FIG. 13A, all vacuum commutation ports 752-1-752-8 of puck 710A are concealed from vacuum channel 766 and associated vacuum acting upon channel 766. As the pucks are rotated clockwise from their position as shown by comparing their position from FIG. 13A to FIG. 13B, first vacuum commutation port 752-8 will be exposed to vacuum channel 766 by rotating past the blockage of stop block 764, activating zone 8. Next, and in sequence, vacuum commutation ports 752-7, 752-6, and 752-5, comprising row R1, will be exposed to vacuum channel 766 by rotating past the blockage of stop block 764, activating their respective zones. Continuing in sequence, as shown in FIG. 13C, vacuum commutation ports 752-4, 752-3, 752-2, and 752-1, comprising row R2, will be exposed to vacuum channel 766 by rotating past the blockage of stop block 762, activating their respective zones. In this fashion, the zones on the puck will have been activated in order, from leading zone 8 to trailing zone 1, linearly and in sequence. By altering the position of stop blocks 762 and 764, the activation pattern can be tailored to expose more or less zones at different times, as desired.

This sequence described immediately above is preferably applied at or before an acquisition point, to achieve the effect demonstrated and discussed with reference to FIG. 4. The article carrying surface 740 of puck 710 receives the discrete object at speed to rotate the discrete object into deposition position. At the deposition position (roughly 6 o'clock in FIG. 7), deposition sequence of vacuum shutoff is initiated on the article carrying surface 740 of the puck 710, leaving the article to be transported free to be placed, deposited, or secondarily transported as desired (for instance by depositing the article to be transported onto a carrier web, or onto a vacuum conveyor). In the deposition sequence, vacuum shutoff is accomplished by passing, in sequence again, commutation ports 752-1-752-8 of puck 710A past stop blocks 762 and 764. The stop blocks 762 and 764 "turn off" zones associated with commutation ports 752-1-752-8 as the commutation ports 752-1-752-8 pass the stop blocks, preventing the vacuum from withdrawing air through the commutation ports 752-1-752-8. The activation/deactivation sequence repeats every rotation, along with, if desired, rotation of every other ear to a desired orientation.

As can be seen in FIG. 7, there can be a period during the revolution where no vacuum is desired at commutation ports 732, after the deposition point (roughly the 6 o'clock position), and prior to the next acquisition point (approximately the 12 o'clock position) in the system during rotation. It is not necessary for the internal manifold 760 to cover portions of the revolution not intended to have vacuum drawn through commutation ports 732, because a vacuum hood (not shown) is configured to cover only the portions of the internal manifold 760 including its channel 766.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. A vacuum porting system comprising:
   an article carrying body comprising an article carrying surface, said article carrying body rotating about an axis;
   a first vacuum commutation zone on said article carrying surface;
   a second vacuum commutation zone on said article carrying surface, adjacent said first vacuum commutation zone on said article carrying surface;
   a first vacuum port coupled to said first vacuum commutation zone; and
   a second vacuum port coupled to said second vacuum commutation zone.

2. A vacuum porting system according to claim 1, said first vacuum port at a first distance from said axis, and said second vacuum port at a second distance from said axis, said second distance greater than said first distance.

3. A vacuum porting system according to claim 1, said vacuum ports coupled to said vacuum commutation zones by a vacuum port manifold.

4. A vacuum porting system comprising:
   an article carrying body comprising an article carrying surface, said article carrying body rotating about an axis;
   a plurality of vacuum commutation zones on said article carrying surface;
   a first array of vacuum ports, said vacuum ports of said first array coupled to a first portion of said plurality of vacuum commutation zones;

a second array of vacuum ports, said vacuum ports of said second array coupled to a second portion of said plurality of vacuum commutation zones;
said first and second arrays of vacuum ports spaced at different radial distances from said axis.

5. A vacuum porting system according to claim 4, said system further comprising a vacuum manifold having an inner surface and an outer surface, said vacuum manifold further comprising a vacuum manifold channel, said vacuum ports selectively exposed to said vacuum manifold channel.

6. A vacuum porting system according to claim 5, said vacuum porting system further comprising a blinder carried by said article carrying body, said blinder coupled to said inner surface of said vacuum manifold during rotation of said article carrying body.

7. A vacuum porting system according to claim 6, said vacuum porting system further comprising a series of article carrying bodies rotating about said axis, said article carrying surfaces extending from a first distance to a second distance from said axis, and a plurality of said vacuum ports and said blinders covering said vacuum manifold channel.

8. A vacuum porting system according to claim 5, said vacuum porting system further comprising a source of vacuum coupled to said outer surface of said vacuum manifold.

9. A vacuum porting system according to claim 5, said vacuum manifold channel presenting a variable width.

10. A vacuum porting system according to claim 4, said first and second arrays of vacuum ports increasing and decreasing radial distances from said axis during rotation of said article carrying bodies about said axis.

11. A vacuum porting system according to claim 1, wherein said article carrying body comprises a plurality of pucks that rotate about said axis.

12. A vacuum porting system according to claim 11, said vacuum porting system further comprising a valve mechanism positioned within each puck of said plurality of pucks and operable to selectively commute a vacuum from said first vacuum port to said first vacuum commutation zone and from said second vacuum port to said second vacuum commutation zone.

13. A vacuum porting system according to claim 11, said vacuum porting system further comprising a vacuum manifold that includes a vacuum manifold channel, wherein said first and second vacuum ports are selectively exposed to said vacuum manifold channel as each said puck of said plurality of pucks rotates past said vacuum manifold channel.

14. A vacuum porting system according to claim 13, said vacuum porting system further comprising a blinder carried by each said puck of said plurality of pucks, said blinder operable to selectively cover said vacuum manifold channel, so as to block the vacuum manifold channel from an ingress of ambient external air.

15. A vacuum porting system comprising:
a turner assembly comprising a plurality of pucks rotating about an axis, each of the plurality of pucks comprising:
an article carrying surface having a plurality of vacuum commutation zones thereon; and
an array of vacuum commutation ports, wherein at least a portion of the array of vacuum commutation ports is fluidly coupled to the plurality of vacuum commutation zones;
an internal manifold in the turner assembly and comprising a vacuum channel to commute a vacuum from the internal manifold to the plurality of pucks as the plurality of pucks rotate past the vacuum channel; and
one or more stop blocks positioned on the turner assembly, wherein the one or more stop blocks act to block fluid coupling between vacuum commutation ports of the array of vacuum commutation ports and the vacuum channel as a respective puck rotates past the vacuum channel, until the vacuum commutation ports rotate past the one or more stop blocks.

16. The vacuum porting system of claim 15 wherein the one or more stop blocks are selectively positionable to change a timing and sequence in which vacuum commutation ports of the array of vacuum commutation ports of a respective puck are fluidly coupled with the vacuum channel.

17. The vacuum porting system of claim 16 wherein the sequence in which vacuum commutation ports of the array of vacuum commutation ports of a respective puck are fluidly coupled with the vacuum channel provides for an ordered activation of the plurality of vacuum commutation zones, from a leading zone of the plurality of vacuum commutation zones to trailing a zone of the plurality of vacuum commutation zones.

18. The vacuum porting system of claim 15 wherein the array of vacuum commutation ports comprises:
a first array of vacuum commutation ports fluidly coupled to a first portion of the plurality of vacuum commutation zones; and
a second array of vacuum commutation ports fluidly coupled to a second portion of the plurality of vacuum commutation zones;
wherein the first and second arrays of vacuum ports spaced at different radial distances from said axis.

19. The vacuum porting system of claim 17 wherein the one or more stop blocks comprises:
a first stop block sized and positioned to selectively cover vacuum commutation ports of the first array of vacuum commutation ports as a respective puck rotates therepast; and
a second stop block sized and positioned to selectively cover vacuum commutation ports of the second array of vacuum commutation ports as a respective puck rotates therepast.

20. The vacuum porting system of claim 15 wherein each of the plurality of pucks further comprises a blinder, the blinder nested within a blinder recess and operable to selectively cover the vacuum channel, so as to block the vacuum channel from an ingress of air external to the turner assembly.

* * * * *